| United States Patent [19]
Ferlazzo et al. | | | [11] 3,933,686
[45] Jan. 20, 1976 |

[54] CATALYST FOR THE PRODUCTION OF ACRYLONITRILE, ACRYLIC ACID AND ACROLEIN

[75] Inventors: Natale Ferlazzo, Milan; Gian Fausto Buzzi, Arona (Novar); Marcello Ghirga, Bresso (Milan), all of Italy

[73] Assignee: Societa' Italiana Resine S.p.A., Milan, Italy

[22] Filed: Nov. 29, 1973

[21] Appl. No.: 420,351

[30] Foreign Application Priority Data
Nov. 30, 1972 Italy .................................. 32280/72

[52] U.S. Cl. .......... 252/467; 260/465.3; 260/465.9; 260/530 N; 260/533 N; 260/604 R
[51] Int. Cl.² ..................... B01J 23/16; B01J 23/64
[58] Field of Search ..................................... 252/467

[56] References Cited
UNITED STATES PATENTS

| | | | |
|---|---|---|---|
| 2,005,645 | 6/1935 | Bond et al. ...................... | 252/467 X |
| 3,380,931 | 4/1968 | Ryland ............................ | 252/467 X |
| 3,414,606 | 12/1968 | Winderl et al. .................. | 252/467 X |
| 3,532,734 | 10/1970 | Anderson et al. ............... | 252/467 X |
| 3,542,842 | 11/1970 | Grasselli et al. ................. | 252/467 X |
| 3,557,199 | 1/1971 | Parthasarathy et al. ......... | 252/467 X |
| 3,579,589 | 5/1971 | Delmon ........................... | 252/467 X |
| 3,642,907 | 2/1972 | Schenach et al. ................ | 252/467 X |
| 3,736,354 | 5/1973 | Yanagita et al. ................. | 252/467 X |
| 3,773,692 | 11/1973 | Hensel et al. .................... | 252/467 X |
| 3,804,903 | 4/1974 | Hagiwara ......................... | 252/467 X |

*Primary Examiner*—Paul F. Shaver
*Attorney, Agent, or Firm*—Sughrue, Rothwell, Mion, Zinn & Macpeak

[57] ABSTRACT

A catalyst suitable for the production of acrylonitrile from propylene or acrolein, acrylic acid from propylene or acrolein, and acrolein from propylene comprising silver oxide and molybdenum oxide in a molar ratio of from about 0.1 to about 2.0.

The catalytic reactions using this new catalyst are directed towards the desired end product by variation of the molar ratio of silver oxide to molybdenum oxide.

1 Claim, No Drawings

CATALYST FOR THE PRODUCTION OF ACRYLONITRILE, ACRYLIC ACID AND ACROLEIN

BACKGROUND OF THE INVENTION

1. Field of the Invention

The present invention relates to a catalyst suitable for the production of acrylonitrile, acrylic acid, and acrolein.

2. Description of the Prior Art catalytically

It is already known in the art that acrolein can be produced by catalytic oxidation of propylene in the gaseous phase with oxygen or with a gas containing molecular oxygen.

It is also known that acrylic acid can be prepared catalytical in the vapor phase from propylene by first oxidizing the propylene to acrolein, separating the acrolein produced, and then oxidizing the acrolein to acrylic acid.

It is also known that acrylic acid can be prepared by direct catalytic oxidation of propylene in the vapor phase and recycling of the acrolein formed as a by-product to the oxidation reactor.

In this case, the mixture that is subjected to oxidation then consists of propylene and acrolein.

It is also known that acrylonitrile can be prepared by catalytic oxidation of propylene or acrolein in the vapor phase with oxygen or a gas containing molecular oxygen in the presence of ammonia.

Various combinations of antimony, arsenic, bismuth, cobalt, molybdenum, rare earths, tin, tellurium, and vanadium, both as oxides and as compounds consisting of at least two of the metals mentioned and oxygen, are normally used as catalysts for the oxidations described.

However, such catalysts have the disadvantage that they are not particularly flexible, in the sense that a catalyst, for example used e.g., for the production of acrylic acid normally cannot also be advantageously used in the production of acrolein or acrylonitrile, or vice versa, even if the relative quantities of the catalytic components are varied.

Moreover, the processes that make use of such catalysts are characterized by the formation of numerous by-products in appreciable quantities, particularly total oxidation products such as water and carbon dioxide.

This naturally means that the selectivities for the desired products are not very high, and they vary widely according to the type of catalyst used and the operating conditions.

SUMMARY OF THE INVENTION

One object of the present invention is a catalyst of high flexibility and high selectivity for the production of acrylonitrile, acrylic acid, and acrolein.

Another object of the present invention is a process for the preparation of such a catalyst.

Other objects will appear from the following description and the examples.

The catalyst of the present invention consists essentially of a mixture of silver and molybdenum oxides in which variation of the molar ratio of these oxides causes preferential displacement towards one or another of the desired products in the catalytic oxidation of propylene or acrolein in the vapor phase.

The use of molybdenum, as an oxide or as a salt, among the catalytic components suitable for the production of acrylonitrile, acrylic acid, and acrolein from propylene and of acrylonitrile and acrylic acid from acrolein is already known in the art.

It is also already known that silver can be used in small quantities as the activator in catalysts comprising at least two catalytically active components such as molybdenum and cobalt, molybdenum and nickel, or molybdenum and bismuth suitable for the oxidation of propylene or acrolein.

In the catalysts known in the art, therefore, molybdenum is never used alone but is always in combination with some other metal such as cobalt, michel, and bismuth, and silver, and if present, is always present as an activator and in a very small quantity.

Moreover, we have already pointed out that the catalysts known in the art for the production of acrylonitrile, acrylic acid, and acrolein are characterized by lack of flexibility and frequently by rather unsatisfactory selectivity values.

On the other hand, we have found a catalyst formed by molybdenum oxide and silver oxide that allows a high selectivity for the desired products and a high flexibility in the oxidation of propylene and of acrolein in the vapor phase.

In other words, we have found a catalyst that in addition to allowing high selectivities for the desired products in the oxidation of propylene or acrolein, enables the oxidation to be preferentially directed towards one or another of these products by variation of the molar ratio of silver oxide to molybdenum oxide.

The composition of the active mixture of oxides thus varies according to the final product desired in the oxidation of propylene or of acrolein.

In general, if all the oxidations are regarded as a single process, the catalyst is active when the molar ratio of silver oxide to molybdenum oxide is in the range of from about 0.1:1 to 2.0:1.

DETAILED DESCRIPTION OF THE INVENTION

In accordance with the present invention, the catalyst is prepared by precipitation from soluble salts of silver and of molybdenum in quantities such as to give the desired molar ratio of silver oxide to molybdenum oxide in the precipitate. The nitrate can be advantageously used as the silver salt, while ammonium molybdate and paramolybdate may be used as salts of molybdenum.

The precipitate obtained is dried at a temperature of from 100° to 130°C for a time in the range of from about 3 to 12 hours.

The catalyst is then activated by heating in a current of air to a temperature in the range of from about 300° to 600°C, this temperature being maintained for a time of not less than 1 hour and preferably in the range of from about 2 to 10 hours.

This treatment may also be carried out directly in the reactor before the introduction of the reactants.

The catalyst in accordance with the invention for the oxidation of propylene and of acrolein may be arranged as a fixed-bed catalyst or as a mobile mass, e.g., flowing as a fluidized bed.

More particularly, in the case of the production of acrylonitrile from propylene or from acrolein, the best results are obtained with a catalyst in which the molar ratio of silver oxide to molybdenum oxide is in the range of from about 0.5:1 to 1.0:1 in the case of propylene and from about 0.25:1 to 0.50:1 in the case of acrolein.

During the reaction of propylene or of acrolein, which is carried out in accordance with one of the known techniques in the vapor phase in the presence of ammonia and oxygen or a gas containing molecular oxygen, temperatures of from about 360° to 450°C and pressures of from about 0.1 to 3 atm are maintained, depending from the reactor used.

The pressure in the reaction vessel is not particularly decisive for the process. The operation is generally carried out at atmospheric pressure or at a slightly higher pressure up to about 2 –3 atm, and particularly at temperatures between about 380° and 420°C.

Under the conditions indicated above, the contact time of the gaseous mixture of propylene or acrolein, oxygen, and ammonia on the catalyst is from 1 to 10 seconds, and preferably from about 2 to 6 seconds in the case of propylene and from 1 to 5 seconds in the case of acrolein.

Variable quantities of inert gases may be added to the reactions gases, whose mutual quantitative ratios are not particularly decisive.

Thus, in accordance with the invention, the operation may be carried out in the presence of inert gases, such as nitrogen, carbon dioxide, or water vapor.

In this way a more uniform temperature distribution is obtained in the reaction vessel and the disadvantages due to overheating are avoided.

The quantity of inert gas used depends on the type and on the shape of the reaction vessel and on the arrangement of the catalyst.

On the other hand, in the case of the production of acrylic acid from propylene or acrolein, the best results are obtained with a catalyst in which the molar ratio of silver oxide to molybdenum oxide is in the range of from about 0.5:1 to 1:1.

The reaction of propylene or acrolein to acrylic acid is carried out according to known methods.

The process is generally carried out at atmospheric pressure or at a slightly higher pressure up to about 2 atm and with a temperature between about 300° and 450°C, and particularly between about 380° and 430°C.

Under these conditions, the best results are obtained when the contact time of the gaseous mixture consisting of propylene or acrolein and oxygen or a gas containing molecular oxygen is in the range from 0.1 to 10 seconds, and preferably from 2 to 6 seconds in the case of propylene and from 0.5 to 5 seconds in the case of acrolein.

Finally, in the production of acrolein from propylene the best results are obtained with a catalyst in which the molar ratio of silver oxide to molybdenum oxide is in the range of from about 0.25:1 to 0.50:1.

The oxidation of propylene may be carried out in accordance with one of the known techniques.

The process is generally carried out at atmospheric pressure or at a slightly higher pressure up to about 3 atm and at a temperature between about 300° and 450°C, and particularly between about 320° and 360°C.

Under these conditions, the best results are obtained when the contact time of the gaseous mixture consisting of propylene and oxygen or a gas containing molecular oxygen is in the range from 0.1 to 10 seconds, and preferably from 1 to 6 seconds.

The invention will now be illustrated by the following examples, which are not intended to limit its scope in any way.

EXAMPLE 1

8.403 g of $(NH_4)_6Mo_7O_{24}.4H_2O$ were dissolved in 80 ml of distilled $H_2O$. 18.485 g of $AgNO_3$ dissolved in 100 ml of water were added dropwise to this solution with stirring.

In this way a suspension of a yellowish-white precipitate was obtained, and this was heated for 1 hour at 80°C and then allowed to settle for 3 hours.

The precipitate was separated by filtration in a Buchner funnel and washed several times with $H_2O$ until nitrates had been completely eliminated.

The product obtained was dried in an oven at 130°C for 3 hours and then activated in a current of air at 500°C for 5 hours.

EXAMPLE 2

The catalyst prepared as in Example 1 was crushed and sieved to obtain the fraction between 50 and 200 microns.

5.5 ml of this catalyst were charged into a tubular AISI 316 steel reactor having a diameter of 12 mm. Using the fixed-bed technique with a temperature of 400°C and at atmospheric pressure, 6.2 liters/hour of a mixture consisting of 10% of $O_2$, 30% of propylene, and 5% of $NH_3$, the remainder being nitrogen (the percentages are by volume), were introduced into the reactor described with a contact time of 3.2 seconds.

The reacted gas was found by analysis to comprise:
1.39% by volume of acrylonitrile
1.60% by volume of acrolein and
4.60% by volume of $CO_2$ The molar selectivity calculated on the reacted propylene was:
32% for acrylonitrile
37% for acrolein
31% for carbon dioxide

EXAMPLE 3

A procedure similar to that of Example 2 was used, except for the temperature, which was 380°C.

The reacted gas was found on analysis to comprise:
1.4% by volume of acrylonitrile
1.4% by volume of acrolein
3.6% by volume of $CO_2$
with a molar selectivity calculated on the reacted propylene of:
35% for acrylonitrile
35% for acrolein
30% for $CO_2$

EXAMPLE 4

1.8 ml of the catalyst of Example 1, crushed and sieved in the range from 50 to 200 microns, were charged into a tubular AISI 316 steel reactor having a diameter of 12 mm.

Using the fixed-bed technique with a temperature of 415°C and at atmospheric pressure, a mixture consisting of 5% by volume of acrolein and 4.3% of oxygen, the remainder being nitrogen, was fed into the reactor described with a contact time of 1.8 seconds.

The reacted gas was found by analysis to comprise:
0.5% by volume of acrylic acid
0.05% by volume of acetic acid
1.8% by volume of a mixture of carbon monoxide and carbon dioxide with a molar selectivity calculated on the reacted acrolein of 45.5% for acrylic acid.

EXAMPLE 5

17.65 g of $(NH_4)_6Mo_7O_{24}\cdot 4H_2O$ were dissolved in 160 ml of distilled $H_2O$. 8.25 g of $AgNO_3$ dissolved in 100 ml of water were added dropwise to this solution with stirring. A suspension of a yellow precipitate was obtained, and this was heated to 80°C for 1 hour and then allowed to settle for 3 hours.

The precipitate was separated by filtration through a Buchner funnel and washed several times with $H_2O$ until nitrates had been completely eliminated.

The product obtained was dried in an oven at 130°C for 3 hours and then activated in a current of air at 320°C for 2 hours.

EXAMPLE 6

The catalyst prepared as in Example 5 was crushed and sieved to collect the fraction between 50 and 200 microns.

5.5 ml of this catalyst were charged into a tubular AISI 316 steel reactor having a diameter of 12 mm. Using the fixed-bed technique with a temperature of 360°C and at atmospheric pressure, a mixture consisting of 30% of propylene and 5.5% of oxygen, the remainder being nitrogen (the percentages are again by volume), was fed to the reactor described with a contact time of 3.2 seconds.

The reacted gas was found on analysis to comprise:
0.975% by volume of acrolein and
1.020% by volume of carbon dioxide
with a molar selectivity calculated on the reacted propylene of 70% for acrolein.

What we claim is:

1. A catalyst for use in the production of acrylonitrile, acrylic acid, and acrolein consisting of silver oxide and molybdenum oxide in a molar ratio of silver oxide to molybdenum oxide in the range of from about 0.1:1 to 2.0:1.

* * * * *